(12) United States Patent
Ishii et al.

(10) Patent No.: US 7,481,996 B2
(45) Date of Patent: Jan. 27, 2009

(54) AEROSOL COSMETIC COMPOSITION

(75) Inventors: Keiko Ishii, Tokyo (JP); Yoshiaki Tanaka, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/911,488

(22) Filed: Aug. 5, 2004

(65) Prior Publication Data

US 2005/0063916 A1    Mar. 24, 2005

(30) Foreign Application Priority Data

Aug. 6, 2003  (JP)  ............................. 2003-287245

(51) Int. Cl.
| | |
|---|---|
| A61K 9/00 | (2006.01) |
| A61K 9/12 | (2006.01) |
| A61K 8/00 | (2006.01) |
| A61K 8/02 | (2006.01) |
| A61K 8/30 | (2006.01) |
| A61K 8/34 | (2006.01) |
| A61K 8/37 | (2006.01) |
| A61K 8/72 | (2006.01) |
| A61K 8/85 | (2006.01) |
| A61K 8/86 | (2006.01) |
| A61K 8/87 | (2006.01) |

(52) U.S. Cl. ...................... 424/70.11; 424/43; 424/45; 424/401; 424/70.1; 424/DIG. 1

(58) Field of Classification Search ............. 424/47, 424/43, 45, 70.11, 70.15, 70.17; 514/724, 514/772.4, 772.6, 772.2

See application file for complete search history.

(56) References Cited

U.S. PATENT DOCUMENTS

| | | | |
|---|---|---|---|
| 4,724,138 A * | 2/1988 | Duffy et al. ................ 424/63 |
| 5,730,963 A | 3/1998 | Hilliard, Jr. et al. | |
| 6,093,410 A * | 7/2000 | Peffly et al. ............... 424/401 |
| 6,126,930 A | 10/2000 | Dubois et al. | |
| 6,328,950 B1 | 12/2001 | Franzke et al. | |
| 6,497,865 B1 * | 12/2002 | Griesbach et al. ........ 424/70.1 |
| 6,596,285 B2 | 7/2003 | Kaneda et al. | |
| 7,012,048 B2 | 3/2006 | Drovetskaya et al. | |
| 2003/0180245 A1 * | 9/2003 | Gotsche et al. ........... 424/70.16 |

FOREIGN PATENT DOCUMENTS

| | | | |
|---|---|---|---|
| DE | 332 69 71 | * | 2/1986 |
| DE | 299 17 773 | * | 2/2000 |
| DE | 10041163 A1 | * | 3/2002 |
| JP | 8092046 A | | 4/1996 |
| JP | 8291032 A | | 11/1996 |
| JP | 9025220 A | | 1/1997 |
| JP | 11071244 A | | 3/1999 |
| JP | 2000159645 A | | 6/2000 |
| JP | 2000204025 A | | 7/2000 |
| JP | 2001505588 W | | 4/2001 |
| JP | 2001181164 A | | 7/2001 |
| JP | 2002302422 | | 10/2002 |
| JP | 2003012477 A | | 1/2003 |
| JP | 2003137752 A | | 5/2003 |
| JP | 2003252730 A | | 9/2003 |
| WO | WO 03/084489 A1 | | 10/2003 |
| WO | WO 2004/030641 A1 | | 4/2004 |

OTHER PUBLICATIONS

Solomons, T. W. G. Organic Chemistry, 5th ed. John Wiley & Sons, Inc.: New York, 1992, p. 402.*
English Language Translation of JP8-92046—Filed with the U.S. Patent and Trademark Office on Oct. 19, 2006.

* cited by examiner

*Primary Examiner*—Johann R Richter
*Assistant Examiner*—James Henry Alstrum-Acevedo
(74) *Attorney, Agent, or Firm*—Oblon, Spivak, McClelland, Maier & Neustadt, P.C.

(57) ABSTRACT

Provided is an aerosol cosmetic composition containing, in a pressure container, a stock solution containing (A) 0.5 to 10 wt. % of a hair styling polymer, (B) 1 to 25 wt. % of a solvent having at least 2 hydroxy groups, having a molecular weight of 62 or greater but not greater than 1000 and being in the liquid form at 30° C., (C) 0.1 to 20 wt. % of a nonionic surfactant having an HLB of from 2.8 to 20 and being in the liquid form at 30° C. and/or N-acetyl ethanolamide, and (D) ethanol and/or water, and (B) a propellant, a weight ratio of the components (A)/(B) falling within a range of from 0.42 to 2.3.

In the aerosol cosmetic composition of the present invention, hair is able to acquire a soft and light finish and moreover, can be re-styled.

17 Claims, No Drawings

AEROSOL COSMETIC COMPOSITION

FIELD OF THE INVENTION

The present invention relates to an aerosol cosmetic composition capable of giving hair soft and light hold, sustaining the finished hairstyle for long hours, and at the same time re-styling the hair into its original coiffure by combing it with fingers or a brush even after the original coiffure is broken.

BACKGROUND OF THE INVENTION

When conventional hair sprays are used, a large amount of a hair styling polymer is usually sprayed to hair to fix it therewith. In this method, however, the polymer fixes hair strands in a bundle so that people using it feel dissatisfied with a stiff or hard feel of the hair treated therewith. In addition, when the fixed point is once broken by combing the hair with fingers or a brush after hairstyling, the hair cannot be restored to its original coiffure. As a hair spray capable of styling hair without stiffness, a hair spray containing fixing polymer and a plasticizer, the latter being added to control the glass transition point of the polymer, is proposed (refer to JP-A-07-145023). This hair spray, however, does not permit re-styling of the hair, because the adhesion of a film formed on the hair surface is insufficient.

Styling agents such as hair wax hold styles by an adhesive force of oil contained therein, so natural and non-sticky finish can be obtained. The adhesive power of the oil is, however, much weaker than the sticking power of a hair styling polymer, so it is therefore difficult to maintain the desired style. Hair styling making use of the adhesive power of the oil cannot sustain a soft and natural finish although the original coiffure can be restored by combing it with fingers or a brush. A hair cosmetic composition containing adhesive components including both a polymer compound and an oily component and thereby having an adhesive power exceeding a certain level is proposed as a composition capable of giving hair a natural hold without firmly setting hair and being excellent in hair style retention (JP-A-11-116443). This composition is, however, accompanied with the drawbacks that re-styling property is low owing to insufficient adhesion and the hair cannot acquire a soft and light finish even after treated with the composition.

SUMMARY OF THE INVENTION

The present invention provides an aerosol cosmetic composition containing, in a pressure container, a stock solution containing the following components (A) to (D):

(A) 0.5 to 10 wt. % of a hair styling polymer, (B) 1 to 25 wt. % of a solvent having at least 2 hydroxy groups, having a molecular weight of 62 or greater but not greater than 1000 and being in the liquid form at 30° C., (C) 0.1 to 20 wt. % of a nonionic surfactant having an HLB of from 2.8 to 20 and being in the liquid form at 30° C. and/or N-acetyl ethanolamide, and (D) ethanol and/or water, and (E) a propellant, a weight ratio of the said components (A)/(B) falling within a range of from 0.42 to 2.3.

DETAILED DESCRIPTION OF THE INVENITON

The present invention relates to an aerosol cosmetic composition capable of giving hair soft and light hold without firmly setting the hair, sustaining the finished hairstyle for long hours, and re-styling the hair into its original shape by combing it with fingers or a brush even after the original shape is broken.

The present inventors have found that when a stock solution prepared from a composition containing a hair styling polymer and a polyol solvent at a predetermined ratio and further containing a specific plasticizer is sprayed, it forms a tacky film made of fine droplets over the hair and joins individual hairs not by firm sticking but by spot bonding, which enables a soft and light finish and re-styling of the hair. Herein, "stock solution" means a solution that is a mixture of compounds contained in an aerosol cosmetic composition except for a propellant.

Examples of the hair styling polymer as Component (A) include alkylacrylamide/acrylate/alkylaminoalkylacrylamide/polyethylene glycol methacrylate copolymers as described in JP-A-02-180911, alkylacrylamide/alkylaminoalkylacrylamide/polyethylene glycol methacrylate copolymers as described in JP-A-08-291206, (methacryloyloxyethylcarboxybetaine/alkyl methacrylate) copolymers such as "Yukaformer R205" (product of Mitsubishi Chemical) and "RAM Resin" (product of Osaka Organic Chemical Industry), (acrylates/lauryl acrylate/stearyl acrylate/ethylamine oxide methacrylate) copolymers such as "DIAFORMER Z-712" (product of Mitsubishi Chemical), (vinylamine/vinyl alcohol) copolymers such as "DIAFIX C-601" (product of Mitsubishi Chemical), acrylic resin alkanolamine solution such as "Plascize L-9540B" (product of Goo Chemical), acrylic acid/acrylamide/ethyl acrylate copolymers such as "ULTRAHOLD 8" and "ULTRAHOLD STRONG" (each, product of BASF), alkyl acrylate/methacrylic acid/silicone copolymer solution such as "LUVIFLEX SILK" (product of BASF), polyurethane-1 such as "LUVISET P.U.R." (product of BASF), polyvinylcaprolactam such as "LUVISKOL PLUS" (product of BASF), alkyl acrylate copolymers such as "LUVIMER 100P" and "LUVIMER 30E" (each, product of BASF), (octylacrylamide/hydroxypropyl acrylate/butylaminoethyl methacrylate) copolymers such as "AMPHOMER SH-701", "AMPHOMER 28-4910", "AMPHOMER LV-71" and "AMPHOMER LV-47" (each, product of National Starch & Chemicals), (alkyl acrylate/octylacrylamide) copolymers such as "AMPHOMER V-42" (product of National Starch & Chemicals), (VA/crotonic acid/vinyl neodecanoate) copolymers such as "Resyn 28-2930" (product of National Starch & Chemicals), polyurethane-14.AMP-acrylates copolymers such as "DYNAMX" (product of National Starch & Chemicals), polyquaternium-11 such as "GAFQUAT 440" (product of ISP), polyquatanium-28 such as "GAFQUAT HS-100" (product of ISP), (vinyl methyl ether/ethyl maleate) copolymers such as "Gantrez ES-225" (product of ISP), (PVP/vinylcaprolactam/DMAPA acrylate) copolymers such as "AQUAFLEX SF-40" (product of ISP), (isobutylene/ethylmaleimide/hydroxyethylmaleimide) copolymers such as "AQUAFLEX FX-64" (product of ISP), polyquaternium-55 such as "STYLEZE W-20" (product of ISP), (vinylpyrrolidone/DMAPA acrylate) copolymers such as "STYLEZE CC-10" (product of ISP), and (vinylpyrrolidone/VA) copolymers such as "PVP/VA735" (product of ISP).

As Component (A), two or more of these hair styling polymers can be used in combination. Its content in the stock solution of the aerosol cosmetic composition of the present invention ranges from 0.5 to 10 wt. %, preferably from 1 to 8 wt. %, more preferably from 1.5 to 7 wt. % in order to give hair a soft and light finish by spot bonding of individual hairs and maintaining the style achieved.

The solvent as Component (B) has at least two hydroxy groups, has a molecular weight of 62 or greater but not greater than 1000 and is in the liquid form at 30° C. Its molecular weight is preferably 90 or greater but not greater than 600, more preferably 100 or greater but not greater than 200. Specific examples include propylene glycol (molecular weight: 76.1), 1,3-butylene glycol (molecular weight: 90.1), glycerin (molecular weight: 92.1), isopentylene glycol (molecular weight: 104.1), hexylene glycol (molecular weight: 118.2), dipropylene glycol (molecular weight: 134.2), polypropylene glycol (polymerization degree: 9, molecular weight: 540) and polyethylene glycol 600. Of these, solvents having at least 4 carbon atoms are preferred as an adequate adhesion can be achieved, and specific examples of such include dipropylene glycol, polypropylene glycol (polymerization degree: 9, molecular weight: 540) and 1,3-butylene glycol, with dipropylene glycol being more preferred. The term "in the liquid" as used herein means that it has a viscosity of 1000 mPa·s or less as measured by a Brookfield rotary viscometer (Rotor No. 2, rotation speed at 12 rpm, for 60 seconds at 30° C.) (which will equally apply to Component (C)).

As Component (B), two or more of these solvents may be used in combination. Its content in the stock solution of the aerosol composition of the present invention ranges from 1 to 25 wt. %, preferably from 2 to 10 wt. %, more preferably from 4 to 8 wt. %, from the viewpoints of forming, together with Component (A), a tacky film to join the individual hairs and enabling re-styling.

A weight ratio of Component (A) to Component (B), that is, (A)/(B), is preferably adjusted to fall-within a range of from 0.42 to 2.3, more preferably from 0.47 to 2.1, still more preferably from 0.52 to 1.9 from the viewpoint of forming a film having adequate adhesion for achieving a soft and light finish, yet allowing re-styling of the hair.

The nonionic surfactant having HLB of from 2.8 to 20 and being in the liquid form at 30° C. and/or N-acetyl ethanolamide as Component (C) improves miscibility of Components (A) and (B) and functions as a plasticizer of Component (A). Examples of such nonionic surfactant include oleic acid monoglyceride (HLB: 2.8), palm kernel diethanolamide (HLB: 2.9), caprylic acid monoglyceride (HLB: 3.2), sorbitan monooleate (HLB: 4.3), isostearyl glyceryl ether (HLB: 5.0), sorbitan monolaurate (HLB: 8.6), tetraoleic acid polyoxyethylene sorbit (HLB: 10.5), polyoxyethylene sorbitan trioleate (HLB: 11.0), tetraoleic acid polyoxyethylene sorbitol (HLB: 11.8), polyoxyethylene sorbitan monooleate (HLB: 13.3), polyoxyethylene (9) tridecyl ether (HLB: 13.3), polyoxyethylene sorbitan monost-earate (HLB: 14.9), and polyoxyethylene sorbitan monopalmitate (HLB: 15.6). Of these, isostearyl glyceryl ether and polyoxyethylene sorbitan monooleate are preferred. The HLB used herein is a value calculated in accordance with the Griffin method.

As Component (C), two or more of these nonionic surfactants and N-acetyl ethanolamide can be used in combination. Its content in the stock solution of the aerosol cosmetic composition of the present invention is from 0.1 to 20 wt. %, preferably from 0.2 to 10 wt. %, more preferably from 0.3 to 5 wt. %.

A ratio of the content of Component (C) to the sum of the contents of Components (A) and (B), that is, (C)/[(A)+(B)] is adjusted to fall within a range of from 0.05 to 0.5, preferably from 0.06 to 0.3, more preferably from 0.08 to 0.2, in view of enabling a soft and light finish and re-styling of the hair by spot bonding of the individual hairs.

The content of ethanol and/or water as Component (D) in the stock solution of the aerosol cosmetic composition of the present invention preferably falls within a range of from 4 to 98.4 wt. %, more preferably from 30 to 98 wt. %, still more preferably from 50 to 95 wt. %.

In order to achieve a soft and light finish by spot bonding of individual hairs, the stock solution, when injected from the container of the aerosol cosmetic composition of the present invention, desirably takes the form of fine droplets having an average particle size (cumulative volume distribution: 50%) of 10 μm or greater but not greater than 40 μm, preferably not greater than 30 μm at a measurement distance (distance from an injection nozzle) of 15 cm.

In the stock solution of the aerosol cosmetic composition of the present invention, incorporation of a perfume compound as Component (F) selected from a specific compound group is preferred from the viewpoints of masking an odor of the base including an ethanol odor, polymer odor and propellant odor, providing a pleasant fragrance upon application, and durability of the fragrance with a proper intensity. In particular when the stock solution of the aerosol cosmetic composition is sprayed in the form of very fine droplets as described above, the surface area of the solution becomes relatively larger and thus the odor derived from the base seems to become stronger compared with that from the base used in the commonplace hair spray. Addition of a specific perfume compound described below can improve the fragrance of the aerosol cosmetic composition. In the present invention, since the perfume component exists in the tacky film of very fine droplets applied to the hair surface, it emits the fragrance slowly and therefore exhibits excellent durability to ensure long lasting fragrance.

Examples of the perfume compound as Component (F) is selected from limonene, methyl anthranilate, eugenol, octyl aldehyde, nonyl aldehyde, decyl aldehyde, undecyl aldehyde, dodecyl aldehyde, α-hexyl cinnamic aldehyde, coumarin, vanillin, cis-3-hexenol, α-terpineol, γ-undecalactone, α-ionone, β-ionone, α-methylionone, β-methylionone, γ-methylionone, 2-methyl-4-(2,2,3-trimethyl-3-cyclopenten-1-yl)-2-buten-1-ol ("Sandalmysore core", product of Kao Corp.), α-damascone, β-damascone, δ-damascone, α-dynascone, β-dynascone, lilial, linalool, phenylethyl alcohol, benzyl alcohol, citronellol, benzyl acetate, hexyl acetate, benzyl benzoate, methyl jasmonate, 3α, 6, 6, 9α-tetramethyldodecahydronaphtho [2,1-b]furan ("AMBROXAN", product of Kao Corp.), phenoxyethyl alcohol, heliotropin, anisyl acetate, anisylacetone, acetyl eugenol, acetyl isoeugenol, cyclopentadecanolide ("PENTALIDE", product of Soda Aromatic) and cyclohexyl salicylate.

Of the above-described perfume compounds, limonene, eugenol, dodecyl aldehyde, α-hexyl cinnamic aldehyde, coumarin, vanillin, cis-3-hexenol, γ-methylionone, 2-methyl-4-(2,2,3-trimethyl-3-cyclopenten-1-yl)-2-buten-1-ol ("Sandalmysore core", product of Kao Corp.),β-damascone, lilial, linalool, phenylethyl alcohol, benzyl alcohol, citronellol, benzyl acetate, methyl jasmonate, 3α, 6, 6, 9α-tetramethyl-dodecahydronaphtho [2,1-b]furan ("AMBROXAN", product of Kao Corp.), heliotropin and cyclohexyl salicylate are preferred.

The content of the perfume compound as Component (F) in the stock solution of the aerosol cosmetic composition of the present invention preferably ranges from 0.01 to 1.0 wt. %, more preferably from 0.05 to 0.5 wt. %, still more preferably from 0.05 to 0.3 wt. %, still more preferably from 0.1 to 0.3.wt. %.

Examples of another perfume compound which can be added to the stock solution, together with Component (F) include terpinolene, α-pinene, β-pinene, isobutylquinoline, triplal, γ-ionone, α-isomethylionone, allylionone, α-irone, β-irone, γ-irone, α-santalol, citronellal, tuberose, 2-(2,4-dimethyl-3-cyclohexenyl)-5-methyl-5-(1-methylpropyl)-1,3-dioxane ("KARANAL", product of Quest International), p-cresol, olibanum resinoid, geranyl nitrile and 4-methyl-2-(2-methylpropyl)-tetrahydro-2H-4pyranol ("Florosa", product of Quest International).

The perfume composition containing Component (F) can be used after diluted with a diluent. Preferred examples of the diluent include methyl (3-oxo-2-pentylcyclopentyl)acetate, propylene glycols such as propylene glycol and dipropylene glycol, and alcohols such as 3-methoxy-3-methylbutanol.

To the stock solution of the aerosol cosmetic composition of the present invention, various components ordinarily employed for aerosol cosmetic compositions, for example, cationic surfactants, anionic surfactants, nonionic surfactants other than Component (C), amphoteric surfactants, pH regulators, vitamins, proteins, amino acids, crude drugs, antiseptics, ultraviolet absorbers, antioxidants, and colorants can be added as needed.

Examples of the propellant as Component (E) include liquefied petroleum gas (LPG), dimethyl ether (DME), $CO_2$ gas and nitrogen gas, and mixtures thereof. Alternatives for chlorofluorocarbon such as HFC-152a can also be employed. It is preferable that the amount of propellant to be added to the stock solution composed of Components (A) to (D) and optional components is such that the weight ratio of the stock solution to the propellant (i.e., stock solution/propellant) ranges from 5/95 to 80/20, more preferably from 40/60 to 70/30. The pressure in the pressure container is preferably adjusted to from 0.15 to 0.45 MPa at a temperature of 25° C.

In order to spray the stock solution in the form of fine droplets as described above, it is preferred to adjust the viscosity of the stock solution composed of Components (A) to (D) and optional components to fall within a range of from 1 to 12 mPa·s, more preferably from 1 to 8 mPa·s. It is also preferred to satisfy the above-described conditions; namely, the weight ratio of stock solution/propellant, and the pressure in the container. The term "viscosity" used herein means a value measured using a Brookfield viscometer (Rotor with BL adapter, rotation speed at 30 rpm, for 60 sec. at 30° C.). The valve used for the pressure container preferably has a stem diameter of ø 0.33 to 0.46 mm, housing diameter of from ø 0.33 to 0.65 mm×vapor tap diameter from ø 0 to 0.64 mm. In the formulation system containing water, use of a vapor-tap-free valve having a stem diameter of from ø 0.33 to 0.42 mm and housing diameter of from ø 0.33 to 0.42 mm is preferred, while in the non-aqueous formulation system, use of a valve having a stem diameter of from ø 0.40 to 0.46 mm and housing diameter from ø 0.42 to 0.65 mm×vapor tap diameter of from ø 0.33 to 0.46 mm is preferred.

EXAMPLES

In the below-described Examples, the viscosity of the stock solution was measured using a Brookfield viscometer of Toki Sangyo Co., Ltd. (Rotor with BL adapter, rotation speed at 30 rpm for 60 sec, at 30° C.). The average particle size of the sprayed droplets corresponds to 50% cumulative volume distribution when measured (measurement distance: 15 cm) by spraying the solution directly to laser light by using a laser diffraction system particle size diameter distribution measuring apparatus "HELOS SYSTEM" (product of Sympatec GmbH, System-Partikel-Technik) at a measuring range of R4 (focus diameter: 200 mm, viscosity measuring range of from 0.5/1.8 to 350 μm.

Examples 1 and 2, and Comparative Examples 1 to 6

In a conventional manner, a stock solution of a hair spray as shown in Table 1 was prepared using LPG (0.25 MPa, 20° C.) as a propellant, and it was filled in an aerosol container equipped with the below-described valve and button, while setting a stock solution/propellant (weight ratio) at 60/40.

Valve: stem diameter: ø 0.41 mm, housing diameter: ø 0.64 mm×vapor tap diameter: ø 0.41 mm Button: orifice size: ø 0.46 mm (MB, concave) (Precision Valve Japan Co., Ltd.)

The hair spray thus obtained was evaluated for its setting power, re-styling power, stiffness and set retention in accordance with the below-described methods and criteria.

Hair Setting Power (Evaluation method) After a 10 cm long and 2 cm wide hair bundle was wetted with water and towel-dried, it was wound around a rod of 4 cm in diameter, followed by natural drying. The hair spray was then applied to the bundle from a distance of 15 cm and dried at 70° C. for 1 hour. Then, the rod was removed from the hair bundle. The hair bundle was hung vertically while fixing its upper end, and a difference $L_0$ between the height of the upper end and the height of the lower end of the hair just after removal of the rod was measured. Setting power was evaluated in accordance with the below-described equation, where setting power was regarded as 0% when $L_0$=10 cm (i.e., the length of the original, uncurled hair bundle.)

$$\text{Setting power}(\%)=(L-L_0)/L\times100$$

Re-styling Power (Evaluation method) A 10 cm long and 2 cm wide hair bundle was wetted with water and towel-dried. It was then wound around a rod of 4 cm in diameter, followed by natural drying. A hair spray was applied to the hair bundle from a distance of 15 cm. After natural drying at room temperature for 1 hour, the hair bundle was removed from the rod. The hair bundle thus treated was vertically hung while fixing its upper end, and a difference $L_0$ between the height of the upper end and the height of the lower end of the hair just after removal from the rod was measured. The hair bundle was then combed to break the curl and was wound again around a rod of 4 cm in diameter. After natural drying at room temperature for 60 minutes, the hair bundle was removed from the rod. The hair bundle was vertically hung, while fixing its upper end, and a difference $L_{60}$ between the height of the upper end and the height of the lower end of the hair just after removal of the rod was measured. Provided that the length of the hair bundle before winding was L (10 cm), re-styling power was evaluated in accordance with the below-described equation. The re-styling power was regarded as 100% when the second curling achieved the same style as the first curling (i.e., $L_0=L_{60}$.)

$$\text{Re-styling power}(\%)=(L-L_{60})/(L-L_0)\times100$$

Absence of Stiffness (Evaluation method) To an experimental human head model (wig), each hair spray was applied and the degree of stiffness of the hair after drying was organoleptically evaluated by a panel of 10 experts in accordance with the following criteria. An average of the scores is indicated.

Set Retention (Durability of Soft Finish)

(Evaluation) To an experimental human head model (wig), each hair spray was applied for styling the hair. After the head model thus treated was allowed to stand for 6 hours at 25° C. and 65% RH, it was subjected to organoleptic evaluation by a panel of 10 experts in accordance with the following criteria. An average of the scores is indicated.

(Evaluation Criteria)
    5: Excellent
    4: Good
    3: Fair
    2: Poor
    1: Very poor The resulting hair spray formed a tacky film on the hair, and it joined individual hairs to provide a soft and light finish and enabled re-styling of the hair.

The resulting hair spray was organoleptically evaluated by a panel of 2 experts for masking property, emission of a pleasant fragrance upon application and durability of the fragrance in accordance with the below-described methods and criteria. An average of the scores is indicated.

Masking Property (Evaluation method) The hair spray was applied to an experimental human head model (wig) and the fragrance just after application was evaluated in accordance with the following criteria:

TABLE 1

| (Wt. %) | Example 1 | Example 2 | Comparative Example 1 | Comparative Example 2 | Comparative Example 3 | Comparative Example 4 | Comparative Example 5 | Comparative Example 6 |
|---|---|---|---|---|---|---|---|---|
| (A) Hair styling polymer * | 6 | 3 | 6 | 4 | — | 2 | 4 | 2 |
| (B) Dipropylene glycol | 4 | 5 | — | 1 | 4 | 8 | — | — |
| (B) Concentrated glycerin | — | — | — | — | — | — | — | 4 |
| (C) Isostearyl glyceryl ether (HLB5.0) | 1 | 0.5 | — | — | 1 | 0.05 | — | — |
| (D) Anhydrous ethanol | Balance | Balance | Balance | Balance | Balance | Balance | Balance | Balance |
| Isopropyl myristate (Mw270) | — | — | — | — | — | — | 1 | — |
| Lactic acid (90 wt. % aq. soln.) | 0.08 | 0.04 | 0.08 | 0.05 | — | 0.03 | 0.05 | 0.03 |
| Perfume | 0.1 | 0.1 | 0.1 | 0.1 | 0.1 | 0.1 | 0.1 | 0.1 |
| Total | 100 | 100 | 100 | 100 | 100 | 100 | 100 | 100 |
| (A)/(B) | 1.5 | 0.6 | — | 4.0 | — | 0.25 | — | 0.5 |
| (C)/[(A) + (B)] | 0.10 | 0.06 | — | — | 0.25 | 0.005 | — | — |
| Viscosity of stock solution (mPa · s) | 8.7 | 4.1 | 7.8 | 4.9 | 1.2 | 3.2 | 4.7 | 3.0 |
| Average particle size | 29 | 21 | 28 | 23 | 16 | 21 | 23 | 21 |
| Evaluation Setting power | 82 | 82 | 82 | 84 | 62 | 78 | 83 | 75 |
| Re-styling power | 65 | 56 | 50 | 63 | 53 | 53 | 47 | 56 |
| Absence of stiffness | 4.5 | 4.5 | 1.0 | 2.0 | 2.0 | 3.5 | 3.5 | 3.5 |
| Durability of soft finish | 4.5 | 3.5 | 1.5 | 2.5 | 1.0 | 1.5 | 1.5 | 1.5 |

* Synthesized in accordance with the process as described in JP-A-08-291206. t-Butylacrylamide/dimethylacrylamide/dimethylaminopropylacrylamide/methoxypolyethylene glycol (PEG400) methacrylate copolymer <52/24/2/22 (wt. %)>

Example 3

In a conventional manner, a stock solution of a hair spray having the below-described formulation was prepared. The resulting stock solution and LPG (0.25 MPa, 20° C.) as a propellant were filled in an aerosol container similar to that employed in Example 1 at a stock solution/propellant weight ratio=60/40. The stock solution had a viscosity of 8.7 mPa·s and an average particle size of droplets upon spraying of 29 μm.

| | (wt. %) |
|---|---|
| Composition of stock solution | |
| (A) Hair styling polymer*[1] | 6.0 |
| (B) Dipropylene glycol | 4.0 |
| (C) Isostearyl glyceryl ether (HLB 5.0) | 1.0 |
| (D) Anhydrous ethanol | Balance |
| (F) Perfume composition (shown in Tables 2 to 7) | 0.2 |
| (Another component) | |
| Lactic acid (90 wt. % aqueous solution) | 0.08 |

*[1]Synthesized in accordance with the process as described in JP-A-08-291206. t-Butylacrylamide/dimethylacrylamide/dimethylaminopropylacrylamide/methoxypolyethylene glycol (PET400) methacrylate copolymer <52/24/2/22 (wt. %)>

(Evaluation Criteria)
    5: The odor*[2] of the base is completely masked.
    4: The odor of the base is masked well.
    3: The odor of the base is masked sufficiently.
    2: Masking of the odor of the base is insufficient.
    1: Masking of the odor of the base is considerably insufficient.

*[2]: The base odor includes ethanol odor, polymer odor and propellant odor.

Emission of Pleasant Fragrance Upon Application (Evaluation method) The hair spray was applied to an experimental human head model (wig) and the fragrance emitted just after application was evaluated in accordance with the following criteria:
    5: Excellent emission of fragrance
    4: Good emission of fragrance
    3: Fair emission of fragrance
    2: Poor emission of fragrance
    1: Very poor emission of fragrance Durability of Fragrance (Evaluation method) The hair spray was applied to an experimental human head model (wig) and the durability of the fragrance one hour after application was evaluated in accordance with the following criteria:
    5: Strong fragrance has remained
    4: Sufficient fragrance has remained
    3: Slight fragrance has remained 2: Very weak fragrance has remained
1: No fragrance has remained

TABLE 2

Example 3 — Perfume compositions

| (Wt. %) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Limonene | 100 | | | | | | | | | | | | | | |
| Methyl anthranilate | | 100 | | | | | | | | | | | | | |
| Eugenol | | | 100 | | | | | | | | | | | | |
| Octyl aldehyde | | | | 100 | | | | | | | | | | | |
| Nonyl aldehyde | | | | | 100 | | | | | | | | | | |
| Decyl aldehyde | | | | | | 100 | | | | | | | | | |
| Undecyl aldehyde | | | | | | | 100 | | | | | | | | |
| Dodecyl aldehyde | | | | | | | | 100 | | | | | | | |
| α-Hexyl cinnamic aldehyde | | | | | | | | | 100 | | | | | | |
| Coumarin | | | | | | | | | | 100 | | | | | |
| Vanillin | | | | | | | | | | | 100 | | | | |
| cis-3-Hexenol | | | | | | | | | | | | 100 | | | |
| α-Terpineol | | | | | | | | | | | | | 100 | | |
| γ-Undecalactone | | | | | | | | | | | | | | 100 | |
| α-Ionone | | | | | | | | | | | | | | | 100 |
| β-Ionone | | | | | | | | | | | | | | | |
| α-Methylionone | | | | | | | | | | | | | | | |
| β-Methylionone | | | | | | | | | | | | | | | |
| γ-Methylionone | | | | | | | | | | | | | | | |
| Sandalmysore Core | | | | | | | | | | | | | | | |
| α-Damascone | | | | | | | | | | | | | | | |
| β-Damascone | | | | | | | | | | | | | | | |
| δ-Damascone | | | | | | | | | | | | | | | |
| α-Dynascone | | | | | | | | | | | | | | | |
| β-Dynascone | | | | | | | | | | | | | | | |
| Lilial | | | | | | | | | | | | | | | |
| Linalool | | | | | | | | | | | | | | | |
| Phenylethyl alcohol | | | | | | | | | | | | | | | |
| Benzyl alcohol | | | | | | | | | | | | | | | |
| Citronellol | | | | | | | | | | | | | | | |
| Benzyl acetate | | | | | | | | | | | | | | | |
| Hexyl acetate | | | | | | | | | | | | | | | |
| Benzyl benzoate | | | | | | | | | | | | | | | |
| Methyl jasmonate | | | | | | | | | | | | | | | |
| Ambroxan | | | | | | | | | | | | | | | |
| Phenoxyethyl alcohol | | | | | | | | | | | | | | | |
| Heliotropin | | | | | | | | | | | | | | | |
| Anisyl acetate | | | | | | | | | | | | | | | |
| Anisylacetone | | | | | | | | | | | | | | | |
| Acetyl eugenol | | | | | | | | | | | | | | | |
| Acetyl isoeugenol | | | | | | | | | | | | | | | |
| Cyclopentadecanolide | | | | | | | | | | | | | | | |
| Cyclohexyl salicylate | | | | | | | | | | | | | | | |
| Diluent (dipropylene glycol) | | | | | | | | | | | | | | | |
| Total | 100 | 100 | 100 | 100 | 100 | 100 | 100 | 100 | 100 | 100 | 100 | 100 | 100 | 100 | 100 |
| Masking property | 4.0 | 4.5 | 4.5 | 4.5 | 4.5 | 4.5 | 4.5 | 4.5 | 4.0 | 4.5 | 4.5 | 4.5 | 4.0 | 4.5 | 4.0 |
| Emission of fragrance | 4.0 | 4.5 | 4.5 | 4.5 | 4.5 | 4.5 | 4.5 | 4.5 | 4.0 | 4.0 | 4.0 | 4.5 | 4.0 | 4.0 | 4.0 |
| Durability of fragrance | 4.0 | 4.0 | 4.0 | 4.0 | 4.0 | 4.0 | 4.0 | 4.0 | 4.0 | 4.5 | 4.5 | 4.0 | 4.0 | 4.5 | 4.5 |

TABLE 3

Example 3 — Perfume compositions

| (Wt. %) | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| Limonene | | | | | | | | | | | | | | | |
| Methyl anthranilate | | | | | | | | | | | | | | | |
| Eugenol | | | | | | | | | | | | | | | |
| Octyl aldehyde | | | | | | | | | | | | | | | |
| Nonyl aldehyde | | | | | | | | | | | | | | | |
| Decyl aldehyde | | | | | | | | | | | | | | | |
| Undecyl aldehyde | | | | | | | | | | | | | | | |
| Dodecyl aldehyde | | | | | | | | | | | | | | | |
| α-Hexyl cinnamic aldehyde | | | | | | | | | | | | | | | |

TABLE 3-continued

Example 3

| (Wt. %) | \multicolumn{15}{c}{Perfume compositions} |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| Coumarin | | | | | | | | | | | | | | | |
| Vanillin | | | | | | | | | | | | | | | |
| cis-3-Hexenol | | | | | | | | | | | | | | | |
| α-Terpineol | | | | | | | | | | | | | | | |
| γ-Undecalactone | | | | | | | | | | | | | | | |
| α-Ionone | | | | | | | | | | | | | | | |
| β-Ionone | 100 | | | | | | | | | | | | | | |
| α-Methylionone | | 100 | | | | | | | | | | | | | |
| β-Methylionone | | | 100 | | | | | | | | | | | | |
| γ-Methylionone | | | | 100 | | | | | | | | | | | |
| Sandalmysore Core | | | | | 100 | | | | | | | | | | |
| α-Damascone | | | | | | 100 | | | | | | | | | |
| β-Damascone | | | | | | | 100 | | | | | | | | |
| δ-Damascone | | | | | | | | 100 | | | | | | | |
| α-Dynascone | | | | | | | | | 100 | | | | | | |
| β-Dynascone | | | | | | | | | | 100 | | | | | |
| Lilial | | | | | | | | | | | 100 | | | | |
| Linalool | | | | | | | | | | | | 100 | | | |
| Phenylethyl alcohol | | | | | | | | | | | | | 100 | | |
| Benzyl alcohol | | | | | | | | | | | | | | 100 | |
| Citronellol | | | | | | | | | | | | | | | 100 |
| Benzyl acetate | | | | | | | | | | | | | | | |
| Hexyl acetate | | | | | | | | | | | | | | | |
| Benzyl benzoate | | | | | | | | | | | | | | | |
| Methyl jasmonate | | | | | | | | | | | | | | | |
| Ambroxan | | | | | | | | | | | | | | | |
| Phenoxyethyl alcohol | | | | | | | | | | | | | | | |
| Heliotropin | | | | | | | | | | | | | | | |
| Anisyl acetate | | | | | | | | | | | | | | | |
| Anisylacetone | | | | | | | | | | | | | | | |
| Acetyl eugenol | | | | | | | | | | | | | | | |
| Acetyl isoeugenol | | | | | | | | | | | | | | | |
| Cyclopentadecanolide | | | | | | | | | | | | | | | |
| Cyclohexyl salicylate | | | | | | | | | | | | | | | |
| Diluent (dipropylene glycol) | | | | | | | | | | | | | | | |
| Total | 100 | 100 | 100 | 100 | 100 | 100 | 100 | 100 | 100 | 100 | 100 | 100 | 100 | 100 | 100 |
| Masking property | 4.0 | 4.0 | 4.0 | 4.0 | 4.0 | 4.5 | 4.5 | 4.5 | 4.5 | 4.5 | 4.0 | 4.0 | 4.0 | 4.0 | 4.0 |
| Emission of fragrance | 4.0 | 4.0 | 4.0 | 4.0 | 4.0 | 4.5 | 4.5 | 4.5 | 4.5 | 4.5 | 4.0 | 4.0 | 4.0 | 4.0 | 4.0 |
| Durability of fragrance | 4.5 | 4.5 | 4.5 | 4.5 | 4.5 | 4.0 | 4.0 | 4.0 | 4.0 | 4.0 | 4.0 | 4.0 | 4.0 | 4.0 | 4.0 |

TABLE 4

Example 3

| (Wt. %) | \multicolumn{15}{c}{Perfume compositions} |
|---|---|---|---|---|---|---|---|---|---|---|---|---|---|---|---|
| | 31 | 32 | 33 | 34 | 35 | 36 | 37 | 38 | 39 | 40 | 41 | 42 | 43 | 44 | 45 |
| Limonene | | | | | | | | | | | | | | 50 | |
| Methyl anthranilate | | | | | | | | | | | | | | | 50 |
| Eugenol | | | | | | | | | | | | | | | |
| Octyl aldehyde | | | | | | | | | | | | | | | |
| Nonyl aldehyde | | | | | | | | | | | | | | | |
| Decyl aldehyde | | | | | | | | | | | | | | | |
| Undecyl aldehyde | | | | | | | | | | | | | | | |
| Dodecyl aldehyde | | | | | | | | | | | | | | | |
| α-Hexyl cinnamic aldehyde | | | | | | | | | | | | | | | |
| Coumarin | | | | | | | | | | | | | | | |
| Vanillin | | | | | | | | | | | | | | | |
| cis-3-Hexenol | | | | | | | | | | | | | | | |
| α-Terpineol | | | | | | | | | | | | | | | |
| γ-Undecalactone | | | | | | | | | | | | | | | |
| α-Ionone | | | | | | | | | | | | | | | |
| β-Ionone | | | | | | | | | | | | | | | |
| α-Methylionone | | | | | | | | | | | | | | | |
| β-Methylionone | | | | | | | | | | | | | | | |
| γ-Methylionone | | | | | | | | | | | | | | | |
| Sandalmysore Core | | | | | | | | | | | | | | | |
| α-Damascone | | | | | | | | | | | | | | | |

TABLE 4-continued

Example 3

Perfume compositions

| (Wt. %) | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| β-Damascone | | | | | | | | | | | | | | 50 | |
| δ-Damascone | | | | | | | | | | | | | | | 50 |
| α-Dynascone | | | | | | | | | | | | | | | |
| β-Dynascone | | | | | | | | | | | | | | | |
| Lilial | | | | | | | | | | | | | | | |
| Linalool | | | | | | | | | | | | | | | |
| Phenylethyl alcohol | | | | | | | | | | | | | | | |
| Benzyl alcohol | | | | | | | | | | | | | | | |
| Citronellol | | | | | | | | | | | | | | | |
| Benzyl acetate | 100 | | | | | | | | | | | | | | |
| Hexyl acetate | | 100 | | | | | | | | | | | | | |
| Benzyl benzoate | | | 100 | | | | | | | | | | | | |
| Methyl jasmonate | | | | 100 | | | | | | | | | | | |
| Ambroxan | | | | | 100 | | | | | | | | | | |
| Phenoxyethyl alcohol | | | | | | 100 | | | | | | | | | |
| Heliotropin | | | | | | | 100 | | | | | | | | |
| Anisyl acetate | | | | | | | | 100 | | | | | | | |
| Anisylacetone | | | | | | | | | 100 | | | | | | |
| Acetyl eugenol | | | | | | | | | | 100 | | | | | |
| Acetyl isoeugenol | | | | | | | | | | | 100 | | | | |
| Cyclopentadecanolide | | | | | | | | | | | | 100 | | | |
| Cyclohexyl salicylate | | | | | | | | | | | | | 100 | | |
| Diluent (dipropylene glycol) | | | | | | | | | | | | | | | |
| Total | 100 | 100 | 100 | 100 | 100 | 100 | 100 | 100 | 100 | 100 | 100 | 100 | 100 | 100 | 100 |
| Masking property | 4.0 | 4.0 | 4.0 | 4.0 | 4.5 | 4.0 | 4.5 | 4.0 | 4.0 | 4.5 | 4.5 | 4.5 | 4.5 | 4.5 | 4.5 |
| Emission of fragrance | 4.0 | 4.0 | 4.0 | 4.0 | 4.0 | 4.0 | 4.0 | 4.0 | 4.5 | 4.5 | 4.0 | 4.0 | 4.5 | 4.5 | 4.5 |
| Durability of fragrance | 4.0 | 4.0 | 4.0 | 4.0 | 4.5 | 4.0 | 4.5 | 4.0 | 4.0 | 4.0 | 4.0 | 4.5 | 4.5 | 4.5 | 4.5 |

TABLE 5

Example 3

Perfume compositions

| (Wt. %) | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Limonene | | | | | | | | | | | | | | | |
| Methyl anthranilate | | | | | | | | | | | | | | | |
| Eugenol | 50 | | | | | | | | | | | | | | |
| Octyl aldehyde | | 50 | | | | | | | | | | | | | |
| Nonyl aldehyde | | | 50 | | | | | | | | | | | | |
| Decyl aldehyde | | | | 50 | | | | | | | | | | | |
| Undecyl aldehyde | | | | | 50 | | | | | | | | | | |
| Dodecyl aldehyde | | | | | | 50 | | | | | | | | | |
| α-Hexyl cinnamic aldehyde | | | | | | | 50 | | | | | | | | |
| Coumarin | | | | | | | | 50 | | | | | | | |
| Vanillin | | | | | | | | | 50 | | | | | | |
| cis-3-Hexenol | | | | | | | | | | 50 | | | | | |
| α-Terpineol | | | | | | | | | | | 50 | | | | |
| γ-Undecalactone | | | | | | | | | | | | 50 | | | |
| α-Ionone | | | | | | | | | | | | | 50 | | |
| β-Ionone | | | | | | | | | | | | | | 50 | |
| α-Methylionone | | | | | | | | | | | | | | | 50 |
| β-Methylionone | | | | | | | | | | | | | | | |
| γ-Methylionone | | | | | | | | | | | | | | | |
| Sandalmysore Core | | | | | | | | | | | | | | | |
| α-Damascone | | | | | | | | | | | | | | | |
| β-Damascone | | | | | | | | | | | | | | | |
| δ-Damascone | | | | | | | | | | | | | | | |
| α-Dynascone | 50 | | | | | | | | | | | | | | |
| β-Dynascone | | 50 | | | | | | | | | | | | | |
| Lilial | | | 50 | | | | | | | | | | | | |
| Linalool | | | | 50 | | | | | | | | | | | |
| Phenylethyl alcohol | | | | | 50 | | | | | | | | | | |
| Benzyl alcohol | | | | | | 50 | | | | | | | | | |
| Citronellol | | | | | | | 50 | | | | | | | | |
| Benzyl acetate | | | | | | | | 50 | | | | | | | |
| Hexyl acetate | | | | | | | | | 50 | | | | | | |
| Benzyl benzoate | | | | | | | | | | 50 | | | | | |

TABLE 5-continued

Example 3

Perfume compositions

| (Wt. %) | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Methyl jasmonate | | | | | | | | | | | 50 | | | | |
| Ambroxan | | | | | | | | | | | | 50 | | | |
| Phenoxyethyl alcohol | | | | | | | | | | | | | 50 | | |
| Heliotropin | | | | | | | | | | | | | | 50 | |
| Anisyl acetate | | | | | | | | | | | | | | | 50 |
| Anisylacetone | | | | | | | | | | | | | | | |
| Acetyl eugenol | | | | | | | | | | | | | | | |
| Acetyl isoeugenol | | | | | | | | | | | | | | | |
| Cyclopentadecanolide | | | | | | | | | | | | | | | |
| Cyclohexyl salicylate | | | | | | | | | | | | | | | |
| Diluent (dipropylene glycol) | | | | | | | | | | | | | | | |
| Total | 100 | 100 | 100 | 100 | 100 | 100 | 100 | 100 | 100 | 100 | 100 | 100 | 100 | 100 | 100 |
| Masking property | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| Emission of fragrance | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| Durability of fragrance | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |

TABLE 6

Example 3

Perfume compositions

| (Wt. %) | 61 | 62 | 63 | 64 | 65 | 66 | 67 | 68 | 69 | 70 | 71 |
|---|---|---|---|---|---|---|---|---|---|---|---|
| Limonene | | | | | | 10 | | 10 | | 5 | 2 |
| Methyl anthranilate | | | | | | | | | | | 2 |
| Eugenol | | | | | | 10 | | 10 | 10 | 5 | 2 |
| Octyl aldehyde | | | | | | | | | | | 2 |
| Nonyl aldehyde | | | | | | | | | | | 2 |
| Decyl aldehyde | | | | | | | | | | | 2 |
| Undecyl aldehyde | | | | | | | | | | | 2 |
| Dodecyl aldehyde | | | | | | 10 | | | 10 | 5 | 2 |
| α-Hexyl cinnamic aldehyde | | | | | | | 10 | 10 | | 5 | 2 |
| Coumarin | | | | | | 10 | | | | 5 | 2 |
| Vanillin | | | | | | | 10 | 10 | | 5 | 2 |
| cis-3-Hexenol | | | | | | 10 | | | 10 | 5 | 2 |
| α-Terpineol | | | | | | | | | | | 2 |
| γ-Undecalactone | | | | | | | | | | | 2 |
| α-Ionone | | | | | | | | | | | 2 |
| β-Ionone | | | | | | | | | | | 2 |
| α-Methylionone | | | | | | | | | | | 2 |
| β-Methylionone | 50 | | | | | | | | | | 2 |
| γ-Methylionone | | 50 | | | | 10 | 10 | | | 5 | 2 |
| Sandalmysore Core | | | 50 | | | | 10 | 10 | | 5 | 2 |
| α-Damascone | | | | 50 | | | | | | | 2 |
| β-Damascone | | | | | 50 | 10 | | 10 | | 5 | 2 |
| δ-Damascone | | | | | | | | | | | 2 |
| α-Dynascone | | | | | | | | | | | 2 |
| β-Dynascone | | | | | | | | | | | 2 |
| Lilial | | | | | | 10 | | | 10 | 5 | 2 |
| Linalool | | | | | | | 10 | 10 | | 5 | 2 |
| Phenylethyl alcohol | | | | | | 10 | | | 10 | 5 | 2 |
| Benzyl alcohol | | | | | | | 10 | 10 | | 5 | 2 |
| Citronellol | | | | | | 10 | | | 10 | 5 | 2 |
| Benzyl acetate | | | | | | | 10 | 10 | | 5 | 2 |
| Hexyl acetate | | | | | | | | | | | 2 |
| Benzyl benzoate | | | | | | | | | | | 2 |
| Methyl jasmonate | | | | | | | 10 | 10 | | 5 | 2 |
| Ambroxan | | | | | | | 10 | | 10 | 5 | 2 |
| Phenoxyethyl alcohol | | | | | | | | | | | 2 |
| Heliotropin | | | | | | | 10 | | 10 | 5 | 2 |
| Anisyl acetate | | | | | | | | | | | 2 |
| Anisylacetone | 50 | | | | | | | | | | 2 |
| Acetyl eugenol | | 50 | | | | | | | | | 2 |
| Acetyl isoeugenol | | | 50 | | | | | | | | 2 |
| Cyclopentadecanolide | | | | 50 | | | | | | | 2 |
| Cyclohexyl salicylate | | | | | 50 | 10 | | 10 | | 5 | 2 |
| Diluent (dipropylene glycol) | | | | | | | | | | | 14 |

TABLE 6-continued

Example 3

| (Wt. %) | Perfume compositions | | | | | | | | | | |
|---|---|---|---|---|---|---|---|---|---|---|---|
| | 61 | 62 | 63 | 64 | 65 | 66 | 67 | 68 | 69 | 70 | 71 |
| Total | 100 | 100 | 100 | 100 | 100 | 100 | 100 | 100 | 100 | 100 | 100 |
| Masking property | 4.5 | 4.5 | 4.5 | 4.5 | 4.5 | 5.0 | 5.0 | 5.0 | 5.0 | 5.0 | 5.0 |
| Emission of fragrance | 4.5 | 4.5 | 4.5 | 4.5 | 4.5 | 5.0 | 5.0 | 5.0 | 5.0 | 5.0 | 5.0 |
| Durability of fragrance | 4.5 | 4.5 | 4.5 | 4.5 | 4.5 | 5.0 | 5.0 | 5.0 | 5.0 | 5.0 | 5.0 |

TABLE 7

Example 3

| (Wt. %) | Perfume compositions | | | | | | | |
|---|---|---|---|---|---|---|---|---|
| | 72 | 73 | 74 | 75 | 76 | 77 | 78 | 79 |
| Isoamyl acetate | 100 | | | 50 | 50 | | 30 | |
| Ethylene brassylate | | 100 | | 50 | | 50 | 30 | |
| Phenylacetaldehyde | | | 100 | | 50 | 50 | 30 | |
| Diluent (dipropylene glycol) | | | | | | | 10 | 100 |
| Total | 100 | 100 | 100 | 100 | 100 | 100 | 100 | 100 |
| Masking property | 1.0 | 1.0 | 1.0 | 1.5 | 1.5 | 1.5 | 1.5 | 1.0 |
| Emission of fragrance | 1.0 | 1.0 | 1.0 | 1.0 | 1.0 | 1.0 | 1.5 | 1.0 |
| Durability of fragrance | 1.0 | 1.0 | 1.0 | 1.5 | 1.0 | 1.5 | 1.5 | 1.0 |

Example 4

In a conventional manner, a stock solution of a hair spray having the below-described formulation was prepared. The resulting stock solution and LPG (0.25 MPa, 20° C.) as a propellant were filled in an aerosol container similar to that employed in Example 1 at a stock solution/propellant weight ratio=40/60. The stock solution had a viscosity of 5.6 mPa·s and an average particle size of droplets upon spraying was 20 μm.

| Composition of stock solution | (wt. %) |
|---|---|
| (A) "Plascize L-9540B" (40 wt. %, product of Goo Chemical)*1 | 12.5 |
| (B) Hexylene glycol | 3.0 |
| (C) Polyethylene glycol 600 | 1.0 |
| (D) "RHEODOL TW-S120" (HLB: 14.9, product of Kao)*2 | 0.5 |

-continued

| Composition of stock solution | (wt. %) |
|---|---|
| (C) N-acetyl ethanolamide | 0.5 |
| (D) Anhydrous ethanol | Balance |

*1 Acrylic resin alkanolamine solution
*2 Polyoxyethylene sorbitan monostearate (20E.O.)

The resulting hair spray formed a tacky film on the hair. It joined individual hairs to provide a soft and light finish and enabled re-styling of the hair.

A hair spray obtained by adding, to the above-described hair spray formulation, 0.01 wt. % of a perfume composition as shown in Table 8 as Component (F) was subjected to organoleptic evaluation by a panel of experts for masking property, emission of fragrance upon application and durability of fragrance in similar methods and criteria to those employed in Example 3. An average of the scores is indicated.

TABLE 8

Example 4

| (Wt. %) | Perfume composition | | | | | | | | | |
|---|---|---|---|---|---|---|---|---|---|---|
| | 66 | 67 | 68 | 69 | 70 | 71 | 75 | 76 | 77 | 78 |
| Limonene | 10 | | 10 | | 5 | 2 | | | | |
| Methyl anthranilate | | | | | | 2 | | | | |
| Eugenol | 10 | | 10 | 10 | 5 | 2 | | | | |
| Octyl aldehyde | | | | | | 2 | | | | |
| Nonyl aldehyde | | | | | | 2 | | | | |
| Decyl aldehyde | | | | | | 2 | | | | |
| Undecyl aldehyde | | | | | | 2 | | | | |
| Dodecyl aldehyde | 10 | | | 10 | 5 | 2 | | | | |
| α-Hexyl cinnamic aldehyde | | | 10 | 10 | 5 | 2 | | | | |
| Coumarin | 10 | | | | 5 | 2 | | | | |
| Vanillin | | 10 | 10 | | 5 | 2 | | | | |

TABLE 8-continued

Example 4

Perfume composition

| (Wt. %) | 66 | 67 | 68 | 69 | 70 | 71 | 75 | 76 | 77 | 78 |
|---|---|---|---|---|---|---|---|---|---|---|
| cis-3-Hexenol | 10 | | | 10 | 5 | 2 | | | | |
| α-Terpineol | | | | | | 2 | | | | |
| γ-Undecalactone | | | | | | 2 | | | | |
| α-Ionone | | | | | | 2 | | | | |
| β-Ionone | | | | | | 2 | | | | |
| α-Methylionone | | | | | | 2 | | | | |
| β-Methylionone | | | | | | 2 | | | | |
| γ-Methylionone | 10 | 10 | | | 5 | 2 | | | | |
| Sandalmysore Core | | 10 | 10 | | 5 | 2 | | | | |
| α-Damascone | | | | | | 2 | | | | |
| β-Damascone | 10 | | 10 | | 5 | 2 | | | | |
| δ-Damascone | | | | | | 2 | | | | |
| α-Dynascone | | | | | | 2 | | | | |
| β-Dynascone | | | | | | 2 | | | | |
| Lilial | 10 | | | 10 | 5 | 2 | | | | |
| Linalool | | 10 | 10 | | 5 | 2 | | | | |
| Phenylethyl alcohol | 10 | | | 10 | 5 | 2 | | | | |
| Benzyl alcohol | | 10 | 10 | | 5 | 2 | | | | |
| Citronellol | 10 | | | 10 | 5 | 2 | | | | |
| Benzyl acetate | | 10 | 10 | | 5 | 2 | | | | |
| Hexyl acetate | | | | | | 2 | | | | |
| Benzyl benzoate | | | | | | 2 | | | | |
| Methyl jasmonate | | 10 | 10 | | 5 | 2 | | | | |
| Ambroxan | | 10 | | 10 | 5 | 2 | | | | |
| Phenoxyethyl alcohol | | | | | | 2 | | | | |
| Heliotropin | | 10 | | 10 | 5 | 2 | | | | |
| Anisyl acetate | | | | | | 2 | | | | |
| Anisylacetone | | | | | | 2 | | | | |
| Acetyl eugenol | | | | | | 2 | | | | |
| Acetyl isoeugenol | | | | | | 2 | | | | |
| Cyclopentadecanolide | | | | | | 2 | | | | |
| Cyclohexyl salicylate | | 10 | | 10 | 5 | 2 | | | | |
| Isoamyl acetate | | | | | | | 50 | 50 | | 30 |
| Ethylene brassylate | | | | | | | 50 | | 50 | 30 |
| Phenylacetaldehyde | | | | | | | | 50 | 50 | 30 |
| Diluent (dipropylene glycol) | 0 | 0 | 0 | 0 | 0 | 14 | 0 | 0 | 0 | 10 |
| Total | 100 | 100 | 100 | 100 | 100 | 100 | 100 | 100 | 100 | 100 |
| Masking property | 4.5 | 4.5 | 4.5 | 4.5 | 4.5 | 4.5 | 1.0 | 1.0 | 1.0 | 1.0 |
| Emission of fragrance | 4.5 | 4.5 | 4.5 | 4.5 | 4.5 | 4.5 | 1.0 | 1.0 | 1.0 | 1.0 |
| Durability of fragrance | 4.5 | 4.5 | 4.5 | 4.5 | 4.5 | 4.5 | 1.0 | 1.0 | 1.0 | 1.0 |

Example 5

In a conventional manner, a stock solution of a hair spray having the below-described formulation was prepared. The resulting stock solution was filled at a stock solution/DME/HFC152a weight ratio=60/20/20 in an aerosol container equipped with the below-described valve and button. The stock solution had a viscosity of 3.0 mPa·s and an average particle size of droplets upon spraying was 40 μm.

Valve: stem diameter ø 0.33 mm, housing diameter ø 0.33 mm×no vapor tap

Button: orifice diameter ø 0.41 mm (MB, concave) (product of Nippon Precision Valve)

| Composition of stock solution | (wt. %) |
|---|---|
| (A) "Luviskol Plus" (40 wt. %, product of BASF)*1 | 7.5 |
| (B) Dipropylene glycol | 4.0 |
| (B) Propylene glycol | 1.0 |
| (C) "SOFTANOL 90" (HLB: 13.3, product of Nippon Shokubai)*2 | 1.0 |
| (D) Purified water | Balance |
| (D) Anhydrous ethanol | 5.0 |

*1 Polyvinylcaprolactam
*2 Polyoxyethylene tridecyl ether (9E.O.)

The resulting hair spray formed a tacky film on the hair. It joined individual hairs to provide a soft and light finish and enabled re-styling of the hair.

A hair spray obtained by adding, to the above-described hair spray formulation, 1.0 wt. % of a perfume composition as shown in Table 9 as Component (F) was subjected to organoleptic evaluation by a panel of experts for masking property, emission of pleasant fragrance upon application and durability of the fragrance in similar methods and criteria to those employed in Example 3. An average of the scores is indicated.

TABLE 9

| (Wt. %) | Example 5 Perfume composition |||||||||||
|---|---|---|---|---|---|---|---|---|---|---|
| | 66 | 67 | 68 | 69 | 70 | 71 | 75 | 76 | 77 | 78 |
| Limonene | 10 | | 10 | | 5 | 2 | | | | |
| Methyl anthranilate | | | | | | 2 | | | | |
| Eugenol | 10 | | 10 | 10 | 5 | 2 | | | | |
| Octyl aldehyde | | | | | | 2 | | | | |
| Nonyl aldehyde | | | | | | 2 | | | | |
| Decyl aldehyde | | | | | | 2 | | | | |
| Undecyl aldehyde | | | | | | 2 | | | | |
| Dodecyl aldehyde | 10 | | | 10 | 5 | 2 | | | | |
| α-Hexyl cinnamic aldehyde | | | 10 | 10 | 5 | 2 | | | | |
| Coumarin | 10 | | | | 5 | 2 | | | | |
| Vanillin | | 10 | 10 | | 5 | 2 | | | | |
| cis-3-Hexenol | 10 | | | 10 | 5 | 2 | | | | |
| α-Terpineol | | | | | | 2 | | | | |
| γ-Undecalactone | | | | | | 2 | | | | |
| α-Ionone | | | | | | 2 | | | | |
| β-Ionone | | | | | | 2 | | | | |
| α-Methylionone | | | | | | 2 | | | | |
| β-Methylionone | | | | | | 2 | | | | |
| γ-Methylionone | 10 | 10 | | | 5 | 2 | | | | |
| Sandalmysore Core | | 10 | 10 | | 5 | 2 | | | | |
| α-Damascone | | | | | | 2 | | | | |
| β-Damascone | 10 | | 10 | | 5 | 2 | | | | |
| δ-Damascone | | | | | | 2 | | | | |
| α-Dynascone | | | | | | 2 | | | | |
| β-Dynascone | | | | | | 2 | | | | |
| Lilial | 10 | | | 10 | 5 | 2 | | | | |
| Linalool | | 10 | 10 | | 5 | 2 | | | | |
| Phenylethyl alcohol | 10 | | | 10 | 5 | 2 | | | | |
| Benzyl alcohol | | 10 | 10 | | 5 | 2 | | | | |
| Citronerol | 10 | | | 10 | 5 | 2 | | | | |
| Benzyl acetate | | 10 | 10 | | 5 | 2 | | | | |
| Hexyl acetate | | | | | | 2 | | | | |
| Benzyl benzoate | | | | | | 2 | | | | |
| Methyl jasmonate | | 10 | 10 | | 5 | 2 | | | | |
| Ambroxan | | 10 | | 10 | 5 | 2 | | | | |
| Phenoxyethyl alcohol | | | | | | 2 | | | | |
| Heliotropin | | 10 | | 10 | 5 | 2 | | | | |
| Anisyl acetate | | | | | | 2 | | | | |
| Anisylacetone | | | | | | 2 | | | | |
| Acetyl eugenol | | | | | | 2 | | | | |
| Acetyl isoeugenol | | | | | | 2 | | | | |
| Cyclopentadecanolide | | | | | | 2 | | | | |
| Cyclohexyl salicylate | | 10 | | 10 | 5 | 2 | | | | |
| Isoamyl acetate | | | | | | | 50 | 50 | | 30 |
| Ethylene brassylate | | | | | | | 50 | | 50 | 30 |
| Phenylacetaldehyde | | | | | | | | 50 | 50 | 30 |
| Diluent (dipropylene glycol) | 0 | 0 | 0 | 0 | 0 | 14 | 0 | 0 | 0 | 10 |
| Total | 100 | 100 | 100 | 100 | 100 | 100 | 100 | 100 | 100 | 100 |
| Masking property | 5.0 | 5.0 | 5.0 | 5.0 | 5.0 | 5.0 | 1.5 | 1.5 | 1.5 | 1.5 |
| Emission of fragrance | 5.0 | 5.0 | 5.0 | 5.0 | 5.0 | 5.0 | 1.5 | 1.5 | 1.5 | 1.5 |
| Durability of fragrance | 5.0 | 5.0 | 5.0 | 5.0 | 5.0 | 5.0 | 1.5 | 1.5 | 1.5 | 1.5 |

Example 6

In a conventional manner, a stock solution of a hair spray having the below-described formulation was prepared. The resulting stock solution and LPG (0.25 MPa, 20° C.) as a propellant were filled in an aerosol container similar to that employed in Example 1 at a stock solution/LPG weight ratio=50/50. The stock solution had a viscosity of 5.4 mPa·s and an average particle size of droplets upon spraying was 23 μm.

| | (wt. %) |
|---|---|
| Composition of stock solution | |
| (A) Alkylacrylamide/acrylate/alkylaminoalkylacrylamide/ polyethylene glycol methacrylate copolymer*[1] | 4.0 |
| (B) "ADEKA CARPOL DL-30" (product of Asahi Denka)*[2] | 4.0 |
| (B) 1,3-Butylene glycol | 1.0 |
| (C) "Penetol GE-IS" (HLB: 5.0, product of Kao) | 0.5 |
| (D) Anhydrous ethanol | Balance |
| (Another component) | |
| Lactic acid | 0.4 |

*[1]A film forming resin synthesized in accordance with JP-A-02-180911
t-Butylacrylamide/ethyl acrylate/dimethylaminopropyl acrylamide/methoxy-polyethylene glycol (PEG400) methacrylate = 55/20/15/10 (wt. %)
*[2]Polypropylene glycol (polymerization degree: 9)
*[3]Isostearyl glyceryl ether The resulting hair spray formed a tacky film on the hair. It joined individual hairs to provide a soft and light finish and enabled re-styling of the hair.

Example 7

In a conventional manner, a stock solution of a hair spray having the below-described formulation was prepared. The resulting stock solution was filled in an aerosol container similar to that employed in Example 1 at a stock solution/HFC152a weight ratio=72/28. The stock solution had a viscosity of 3.7 mPa·s and an average particle size of droplets upon spraying was 32 μm.

| | (wt. %) |
|---|---|
| Composition of stock solution | |
| (A) "Amphomer SH-701" (30 wt. %, product of National Starch & Chemical)*[1] | 4.15 |
| (A) "Resyn 28-2930" (product of National Starch & Chemical)*[2] | 1.25 |
| (B) Dipropylene glycol | 5.0 |
| (C) "Penetol GE-IS" (HLB: 5.0, product of Kao)*[3] | 3.0 |
| (D) Anhydrous ethanol | Balance |
| (Another component) | |
| Aminomethylpropanol | 0.6 |
| (F) Perfume (Example 3, Perfume composition 66) | 0.1 |

*[1](octylacrylamide/hydroxypropyl acrylate/butylaminoethyl methacrylate) copolymer
*[2](VA/crotonic acid/vinyl neodecanoate) copolymer
*[3]Isostearyl glyceryl ether The resulting hair spray formed a tacky film on the hair. It joined individual hairs to form a soft and light finish and enabled re-styling of the hair.

The invention claimed is:

1. An aerosol cosmetic composition containing, in a pressure container, a stock solution comprising the following components (A) to (D):
    (A) 0.5 to 10 wt. % of a hair styling polymer,
    (B) 1 to 25 wt. % of a solvent having at least 2 hydroxy groups, having a molecular weight of 62 or greater but not greater than 1000 and being in a liquid form at 30° C.,
    (C) 0.1 to 20 wt. % of a nonionic surfactant having an HLB of from 2.8 to 20 and being in a liquid form at 30° C. which is at least one selected from the group consisting of oleic acid monoglyceride, palm kernel diethanolamide, caprylic acid monoglyceride, sorbitan monooleate, isostearyl glyceryl ether, sorbitan monolaurate, tetraoleic acid polyoxyethylene sorbit, tetraoleic acid polyoxyethylene sorbitol and polyoxyethylene (9) tridecyl ether, and
    (D) ethanol and/or water, and
    (E) a propellant, a weight ratio of said components (A)/(B) falling within a range of from 0.42 to 2.3
    wherein said hair styling polymer is at least one selected from the group consisting of alkylacrylamide/acrylate/alkylaminoalkylacrylamide/polyethylene glycol methacrylate copolymers, alkylacrylamide/alkylaminoalkylacrylamide/polyethylene glycol methacrylate copolymers, (methacryloyloxyethylcarboxybetaine/alkyl methacrylate) copolymers, (acrylates/lauryl acrylate/stearyl acrylate/ethylamine oxide methacrylate) copolymers, (vinylamine/vinyl alcohol) copolymers, acrylic resin alkanolamine solution, acrylic acid/acrylamide/ethyl acrylate copolymers, alkyl acrylate/methacrylic acid/silicone copolymer solution, polyurethane-1, polyvinylcaprolactam, alkyl acrylate copolymers, (octylacrylamide/hydroxypropyl acrylate/butylaminoethyl methacrylate) copolymers, (alkyl acrylate/octylacrylamide) copolymers, (VA/crotonic acid/vinyl neodecanoate) copolymers, polyurethane-14·AMP-acrylates copolymers, polyquatanium-28,(vinyl methyl ether/ethyl maleate) copolymers, (PVP/vinylcaprolactam/DMAPA acrylate) copolymers), (isobutylene/ethylmaleimide/hydroxyethylmaleimide) copolymers, polyquaternium-55, and (vinylpyrrolidone/DMAPA acrylate) copolymers,
    wherein a viscosity of said stock solution of component (A) to (D) ranges from 1 to 12 mPa·s
    and wherein an average particle size of droplets formed upon spraying of said stock solution from a container is 10 μm or greater but not greater than 40 μm.

2. The aerosol cosmetic composition of claim 1, wherein a weight ratio of(C)/[(A)+(B)] falls within a range of from 0.05 to 0.5.

3. The aerosol cosmetic composition of claim 1, further comprising, as component (F), at least one perfume compound selected from the group consisting of limonene, methyl anthranilate, eugenol, octyl aldehyde, nonyl aldehyde, decyl aldehyde, undecyl aldehyde, dodecyl aldehyde, α-hexyl cinnamic aldehyde, coumarin, vanillin, cis-3-hexenol, α-terpineol, γ-undecalactone, α-ionone, β-ionone, α-methylionone, β-methylionone, γ-methylionone, 2-methyl-4-(2,2,3-trimethyl-3-cyclopenten-1-yl)-2-buten-1-ol, α-damascone, β-damascone, δ-damascone, α-dynascone, β-dynascone, lilial, linalool, phenylethyl alcohol, benzyl alcohol, citronellol, benzyl acetate, hexyl acetate, benzyl benzoate, methyl jasmonate, 3α, 6, 6, 9α-tetramethyldodecahydronaphtho[2,1-b]furan, phenoxyethyl alcohol, heliotropin, anisyl acetate, anisylacetone, acetyl eugenol, acetyl isoeugenol, cyclopentadecanolide and cyclohexyl salicylate.

4. The aerosol cosmetic composition of claim 3, wherein the content of component (F) in the stock solution ranges from 0.01 to 1.0 wt. %.

5. The aerosol composition of claim 1, wherein component (A) is present in an amount of 1 to 8 wt. %.

6. The aerosol composition of claim 1, wherein component (B) has a molecular weight of 90 or greater but not greater than 600.

7. The aerosol composition of claim 1, wherein component (B) is present in an amount of 4 to 8 wt. %.

8. The aerosol composition of claim 1, wherein said weight ratio of (A)/(B) is 0.47 to 2.1.

9. The aerosol composition of claim 1, wherein component (C) is present in an amount of 0.3 to 5 wt. %.

10. The aerosol composition of claim 1, wherein component (D) is present in an amount of 4 to 98.4 wt. %.

11. The aerosol composition of claim 1, wherein component (D) is present in an amount of 30 to 98 wt. %.

12. The aerosol composition of claim 1, wherein component (D) is present in an amount of 50 to 95 wt. %.

13. The aerosol composition of claim 1, wherein a viscosity of a stock solution of component (A) to (D) ranges from 1 to 8 mPa·s.

14. The aerosol composition of claim 1, wherein a weight ratio of a stock solution of component (A) to (D) to propellant ranges from 5/95 to 80/20.

15. The aerosol composition of claim 1, wherein a pressure in said pressure container is from 0.15 to 0.45 MPa at a temperature of 25° C.

16. The aerosol composition of claim 1, wherein component (D) comprises ethanol.

17. The aerosol composition of claim 1, wherein component (B) is at least one solvent selected from the group consisting of 1,3-butylene glycol (molecular weight: 90.1), isopentylene glycol (molecular weight: 104.1), hexylene glycol (molecular weight: 118.2), dipropylene glycol (molecular weight: 134.2), polypropylene glycol (polymerization degree: 9, molecular weight: 540) and polyethylene glycol 600.

* * * * *